United States Patent [19]

Bauer et al.

[11] Patent Number: 4,594,098

[45] Date of Patent: Jun. 10, 1986

[54] PHOSPHORUS-CONTAINING FUNCTIONAL DERIVATIVES OF ACETIC ACID, PROCESS FOR THEIR PREPARATION AND HERBICIDAL AND GROWTH-REGULATING AGENTS CONTAINING THEM

[75] Inventors: Klaus Bauer, Rodgau; Hermann Bieringer, Eppstein; Helmut Bürstell, Frankfurt am Main; Jean Kocur, Hofheim am Taunus, all of Fed. Rep. of Germany

[73] Assignee: Hoechst Aktiengesellschaft, Frankfurt, Fed. Rep. of Germany

[21] Appl. No.: 755,546

[22] Filed: Jul. 16, 1985

Related U.S. Application Data

[63] Continuation of Ser. No. 530,196, Sep. 7, 1983.

[30] Foreign Application Priority Data

Sep. 10, 1982 [DE] Fed. Rep. of Germany ....... 3233603
Oct. 21, 1982 [DE] Fed. Rep. of Germany ....... 3238958

[51] Int. Cl.⁴ .................. A01N 57/22; A01N 57/20; C07C 69/675
[52] U.S. Cl. ........................................... 71/86; 71/87; 558/385; 560/12; 560/24; 560/29; 560/32; 560/33; 560/60; 560/132; 560/137; 560/144; 560/145; 560/148; 560/150; 560/151; 560/157; 560/160; 560/162; 560/163; 560/165; 560/179; 560/187; 560/188; 560/189; 562/470; 562/579; 562/588; 564/150; 564/151
[58] Field of Search .................. 560/12, 24, 29, 32, 560/33, 132, 137, 144, 145, 150, 151, 162, 163, 165, 189; 562/588; 564/150

[56] References Cited

U.S. PATENT DOCUMENTS 4,225,521  9/1980  Sauers ................................ 560/226

FOREIGN PATENT DOCUMENTS 0001331   4/1979  European Pat. Off. .
2111672   9/1972  Fed. Rep. of Germany .
2717440  12/1977  Fed. Rep. of Germany .

OTHER PUBLICATIONS

Chemical Abstracts, vol. 71, No. 13, Sep. 29, 1969, p. 474, citation 61477y.

*Primary Examiner*—Natalie Trousof
*Assistant Examiner*—Bruce D. Gray
*Attorney, Agent, or Firm*—Curtis, Morris & Safford

[57] ABSTRACT

Compounds of the formula

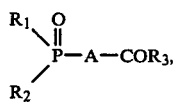

in which $R_1$ and $R_2$ denote alkyl, $CF_3$, benzyl cyclohexyl, cyanoethyl, phenyl or OH and A denotes, inter alia, the groups —CO—, CHOH or CH—$NH_2$ and —$COR_3$ denotes a carboxyl, carboxylic ester or carboxamido group, are active herbicides.

13 Claims, No Drawings

PHOSPHORUS-CONTAINING FUNCTIONAL DERIVATIVES OF ACETIC ACID, PROCESS FOR THEIR PREPARATION AND HERBICIDAL AND GROWTH-REGULATING AGENTS CONTAINING THEM

This application is a continuation of application Ser. No. 530,196, filed Sept. 7, 1983.

Phosphonoglycine of the formula $(HO)_2P(O)CH(NH_2)COOH$ is described as a compound with herbicidal properties in Japanese Application 54.089,027. It has now been found that numerous other phosphorus-containing functional derivatives of acetic acid have an excellent herbicidal and growth-regulating action.

The invention relates to compounds of the general formula

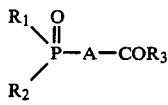

in which

R$_1$ and R$_2$ independently of one another denote $(C_1-C_{10})$-alkyl, $CF_3$, benzyl, cyclohexyl, cyanoethyl, phenyl or OH; A denotes a group —CO—, —CHOH, —CHOR$_4$, —CHHal, —CHOCONR$_5$R$_6$ or —CHNHR$_7$;

R$_3$ denotes —OH, —SH, $(C_1-C_{12})$-alkoxy, $(C_3-C_8)$-cycloalkoxy, $(C_3-C_6)$-alkenyloxy, $(C_3-C_6)$-alkynyloxy, phenoxy or benzyloxy, it being possible for the groups mentioned in turn to be substituted by OH, halogen, $CF_3$, $(C_1-C_4)$-alkyl or $(C_1-C_4)$-alkoxy; $(C_1-C_6)$-alkylthio, $(C_3-C_8)$-cycloalkylthio, $(C_3-C_6)$-alkenylthio, $(C_3-C_6)$-alkynylthio, phenylthio or benzylthio, it being possible for the groups mentioned in turn to be substituted by halogen, $CF_3$, $(C_1-C_4)$-alkyl or $(C_1-C_4)$-alkoxy; amino, $(C_1-C_4)$-alkylamino, hydroxylamino, O-$(C_1-C_4)$-alkylhydroxylamino, di-$(C_1-C_4)$-alkylamino, anilino, $(C_7-C_{10})$-phenylalkylamino, di-$(C_7-C_{10})$-phenylalkylamino, N-phenyl-N-$(C_1-C_4)$-alkylamino, N-phenyl-N-$(C_3-C_6)$-alkenylamino or N-phenyl-N-$(C_3-C_6)$-alkynylamino, it being possible for the groups mentioned in turn to be substituted by OH, halogen, $(C_1-C_4)$-alkyl or $(C_1-C_4)$-alkoxy; hydrazino, β-$(C_1-C_4)$-alkylhydrazino, β,β-di-$(C_1-C_4)$-alkylhydrazino, piperidino, pyrrolidino, morpholino, 2,6-dimethylmorpholino or a radical of the formula

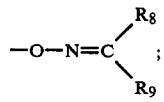

R$_4$ denotes $(C_1-C_6)$-alkyl, allyl, propargyl, benzyl or halogenobenzyl;

R$_5$ and R$_6$ independently of one another denote hydrogen, $(C_1-C_{12})$-alkyl, $(C_3-C_8)$-cycloalkyl, $(C_3-C_6)$-alkenyl, $(C_3-C_6)$-alkynyl, phenyl, benzyl, benzoyl, phenoxysulfonyl, $(C_1-C_{12})$-alkylsulfonyl, $(C_3-C_6)$-alkenylsulfonyl or phenylsulfonyl, it being possible for the groups mentioned in turn to be substituted by halogen, $CF_3$, CN, $(C_1-C_4)$-alkoxy or $(C_1-C_4)$-alkoxycarbonyl;

R$_7$ denotes hydrogen, $(C_1-C_6)$-alkyl, $(C_2-C_6)$-alkenyl, $(C_3-C_6)$-alkynyl, $(C_1-C_4)$-acyl, halogeno-$(C_1-C_4)$-acyl or benzoyl; and R$_8$ and R$_9$ independently of one another denote $(C_1-C_{12})$-alkyl; or together denote an alkylene radical with 3–8 carbon atoms, and salts thereof with bases or acids, with the proviso that R$_1$ and R$_2$ may not simultaneously be —OH if A represents a group of the formula

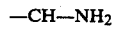

In the above text, "Hal" or "Halogen" preferably denotes chlorine or bromine. If they are substituted, the aliphatic groups mentioned for R$_3$ are preferably monosubstituted by hydroxyl, $(C_1-C_4)$-alkoxy or halogen, in particular chlorine. The aromatic groups can be mono-, di- or tri-substituted, preferably by halogen, in particular by chlorine, or by $CF_3$, $(C_1-C_2)$-alkyl or $(C_1-C_2)$-alkoxy.

If one of the radicals R$_1$, R$_2$ or R$_3$ denotes —OH or if R$_3$ denotes —SH, the compounds of the formula I are also capable of salt formation with inorganic and organic bases. Examples of possible base cations are Na$^+$, K$^+$, NH$_4^+$, Ca$^{2+}$, Mg$^{2+}$, Zn$^{2+}$, Cu$^{2+}$, Fe$^{2+}$, Ni$^{2+}$, $(C_1-C_4)$-alkyl-NH$_3^+$, di-$(C_1-C_4)$-alkyl-NH$_2^+$, tri-$(C_1-C_4)$-alkyl-NH$^+$ or $(HOCH_2CH_2)_3NH^+$.

If A represents the group —CH—NH$_2$, the compounds of the formula I can also form salts with inorganic or organic acids having a dissociation constant $>10^{-3}$. Strong mineral acids, such as HCl, HBr or H$_2$SO$_4$, are particularly suitable for salt formation.

The following radicals, for example, are suitable for R$_1$ to R$_3$ and A:

R$_1$ and R$_2$: CH$_3$, C$_2$H$_5$, C$_4$H$_9$, CF$_3$, OH, ONa, OK and ONH$_4$;

R$_3$: OH, ONH$_4$, ONa, OK, OCH$_3$, OC$_2$H$_5$, OCH$_2$CH$_2$Cl, OCH$_2$CH$_2$OH, OC$_4$H$_9$(n), OCH$_2$CHClCH$_2$Cl, OCH$_2$CH$_2$CH$_2$OH, OCH$_2$CF$_3$, OCH$_2$CH$_2$OCH$_3$, OCH$_2$CH=CH$_2$, OCH$_2$C≡CH, OC$_6$H$_5$, OC$_6$H$_4$Cl(p), OC$_6$H$_4$CH$_3$(p), OC$_6$H$_3$Cl$_2$(o, p), OCH$_2$C$_6$H$_5$, OCH$_2$C$_6$H$_5$CH$_3$(p), cyclohexyloxy and cyclopentyloxy; SH, SC$_2$H$_5$, SCH$_2$CH=CH$_2$, SC$_6$H$_5$; NH$_2$, NHCH$_3$, NHC$_4$H$_9$(n), NHCH$_2$CH$_2$OH, N(CH$_3$)$_2$, N(C$_2$H$_5$)$_2$, NHOH, NHOCH$_3$, NHOC$_4$H$_9$(n), N(i-C$_3$H$_7$)$_2$, NHC$_6$H$_5$, NH—C$_6$H$_4$Cl(p), NH—C$_6$H$_4$CH$_3$(p), NHCH$_2$C$_6$H$_5$, NHCH$_2$CH$_2$C$_6$H$_5$, N(CH$_3$)C$_6$H$_5$, N(CH$_3$)C$_6$H$_5$Br, NH—C$_6$H$_5$OCH$_3$(p), NHNH$_2$, NHNHCH$_3$ and NHN(C$_2$H$_5$)$_2$; and ON=C(CH$_3$)$_2$;

A: CHOC$_2$H$_5$, CHOC$_3$H$_7$(i), CHOCH$_2$CH=CH$_2$, CHOCH$_2$C≡CH, CHOCH$_2$—C$_6$H$_4$Cl(p), CHOCH$_2$C$_6$H$_3$Cl$_2$(o,p), CHOCH$_2$C$_6$H$_4$Br(p), CHOCONH$_2$, CHOCONHCH$_3$, CHOCON(CH$_3$)$_2$, CHOCONHSO$_2$CH$_3$, CHOCONHSO$_2$CH$_2$C≡CHCH$_3$, CHOCON(CH$_2$=CH$_2$)$_2$, CH$_2$OCONHC$_6$H$_5$, CHCl, CHBr, CHNH$_2$, CHNHC$_4$H$_9$(n), CHN(C$_2$H$_5$)$_2$, CHNHCHO, CHNHCOCH$_3$ and CHNHCOCF$_3$.

The preparation processes comprise (a) for the preparation of compounds in which $$A = -\overset{|}{C}=O,$$

reacting compounds of the formula $$R_1'-P\begin{matrix}O(C_1-C_4)Alkyl\\ \\O(C_1-C_4)Alkyl\end{matrix} \quad (II)$$

or $$\begin{matrix}R_1'\\ \\R_2'\end{matrix}P-O(C_1-C_4)Alkyl \quad (III)$$

in which $R_1$, and $R_2$, denote $(C_1-C_{10})$-alkoxy or have one of the meanings of $R_1$ and $R_2$ respectively (with the exception of OH), with oxalic acid ester halides of the formula $$Hal-CO-COO(C_1-C_4)alkyl \quad (IV)$$

or (b) for the preparation of compounds in which $$A = -\overset{|}{C}HOH \text{ or } -\overset{|}{C}HNH_2,$$

reacting compounds of the formula $$\begin{matrix}R_1''\\ \\R_2''\end{matrix}\overset{O}{\underset{\|}{P}}H \quad (V)$$

in which $R_1''$ and $R_2''$ denote $(C_1-C_{10})$-alkoxy or have the meaning of $R_1$ and $R_2$ respectively, with compounds of the formula $$X=CH-COR_3 \quad (VI)$$

in which X denotes =O, =NH or =N—$R_{10}$ and $R_{10}$ denotes benzyl, benzhydryl, trityl, —N[$(C_1-C_3)$alkyl]$_2$, —NHC$_6$H$_5$ or —NHCOO($C_1-C_4$)alkyl and any radical $R_{10}$ present is split off by hydrogenolysis or hydrolysis; or (c) converting the compounds of the formula $$\begin{matrix}R_1\\ \\R_2\end{matrix}\overset{O}{\underset{\|}{P}}-\underset{\underset{XH}{|}}{CH}-COR_3 \quad (VII)$$

obtained according to (b) into other compounds of the formula I by alkylation, halogenation, benzylation, oxidation, acylation or amination, and, if desired, hydrolyzing alkoxy groups in position $R_1$ or $R_2$ or converting acids into their salts.

Re (a): The starting substances of the formulae II and III are known from the literature (c.f. Houben-Weyl, Methoden der org. Chemie (Methods of Organic Chemistry) Volume XII/1, 208, 324 and Volume XII/2, 53), or they can be prepared in an analogous manner. The reaction with the compounds IV can be carried out with or without the addition of a solvent, at temperatures from 20° to 100° C.; if appropriate, suitable solvents are inert solvents, such as dioxane, tetrahydrofuran, acetonitrile, dimethoxyethane, methylene chloride and toluene.

Re (b): The starting substances of the formula V are also known (c.f. German Offenlegungsschrift 1,793,203 and Houben-Weyl Volume XII/1, 193), or they can be prepared in an analogous manner. Some of the compounds of the formula VI are known (c.f. Houben-Weyl Volume VII, 217 and 280; Ber. 37, 3190 (1904); Ann. 690, 138 (1965)), or they can be prepared in a corresponding manner. Hydrogen in the presence of palladium-on-charcoal, as the catalyst, is used for splitting off a radical $R_{10}$ by hydrogenolysis (for example Synthesis 1980, 1028–32). The solvents are the same as for (a), with the addition of ethyl acetate, and the reaction temperatures are between 0° and 100°, preferably 10° and 30°. In some cases it is appropriate to accelerate the reaction by adding bases; suitable bases are alkali metal hydroxides or alcoholates, such as NaOH, KOH, NaOCH$_3$ and KO-tert.-butyl, and also tertiary nitrogen bases, such as triethylamine or methyl diisopropylamine.

Re (c): Compounds of the formula VII in which X represents oxygen can be converted, in a generally known manner by means of isocyanates of the formula $R_4$—N=C=O or chloroformylamines of the formula $R_4R_5N$—COCl, into the end products of the formula I in which A=—CH—OCONR$_4$R$_5$, R$_5$ being H if isocyanates are used. The corresponding halogen compounds (A=—CHHal) are obtained from VII with halogenating agents, such as PCl$_5$, PCl$_3$, PBr$_3$ or SOCl$_2$. These halogen compounds can in turn be converted into the corresponding amino compounds (A=—CHNH$_2$) by known processes, such as, for example, the Gabriel synthesis. Alkylation, acylation or benzylation on the group —XH leads to compounds in which A=—CHO(C$_2$-C$_6$)alkyl, —CHO(halogen)benzyl or —CHNHR$_6$ (in which R$_6$ is other than H). The compounds of the formula I in which A=CO can also be obtained from VII (X=O) by oxidation, for example with chromium trioxide. All these reactions are well-known to the expert and need no further explanation.

As can be seen from the formula VII, a center of asymmetry is obtained on addition of the phosphorus compounds V onto the compounds of the formula VI. The compounds of the formula I can therefore be in the form of optical isomers, to which the invention also relates.

The compounds according to the invention have an excellent and very broad herbicidal action against a wide spectrum of annual and perennial gramineaceous weeds and broad-leaved weeds at verges, on industrial land or on railway land. The invention thus also relates to herbicidal agents containing the compounds of the formula I, and their use for combating undesirable plant growth.

The active compounds are suitable both for use in agriculture and for combating weeds. They can be used in annual or perennial agricultural crops as long as it is ensured, by the type of application and/or the age of the crop plants, that the crop plants and their sensitive green parts do not suffer damage. Examples of such possible uses are plantations, tree crops, vineyards and the like.

Since application of the novel compounds in useful crops before emergence of the crop plants causes only little or no damage, they can be used against weeds even before emergence of the seed or before sowing or after harvesting.

However, the compounds according to the invention can also be used against plant growth of the useful plants (for example cotton or potatoes) themselves where this growth interferes with harvesting.

Typical growth-regulating effects can also be achieved with the novel compounds, depending on the dose applied; thus, for example, the growth of the plants and also the amount of undesirable plant contents can be influenced. The compounds are therefore suitable as growth regulators in crops of useful plants, such as, for example, cereal, maize, sugar cane, tobacco, rice and sorghum. On the other hand, plant areas, for example cultivated lawns, or plant communities at verges and roadsides as well as ornamental plants can also be regulated.

The vegetative growth of a number of monocotyledon and dicotyledon plants is inhibited by application of the compounds according to the invention, and as a consequence thereof, inter alia, the carbohydrate content in the plants or their fruits is increased. The result of this is frequently a positive influencing of the amount of desirable plant contents, such as proteins or carbohydrates (starch and sugar).

For example, the sucrose content is increased in sugar cane and sugar beet and the levulose content is increased in fruit and grapes; in other plants, such as potatoes, maize, millet (sorghum) and green forage (clover and lucerne), the starch content increases. The advantages thereby achieved are evident, and require no explanation.

Application takes place about one week to 5 months before the harvest. When this period has elapsed, the degree of ripening, caused by the active compounds, and hence also the carbohydrate content has reached a maximum. Generally, it should be remembered that the growth rate and duration of vegetation of the crops can vary within considerable limits. Sugar cane, for example, requires 1-3 years to reach harvesting ripeness, depending on the location and climate. The time of application must also be varied accordingly. For sugar cane this can be, for example, 1 to 13 weeks before the harvest.

The agents can be used as wettable powders, emulsifiable concentrates, sprayable solutions, dusting agents, dressing agents, dispersions, granules or microgranules in the usual formulations.

Wettable powders are products which can be dispersed uniformly in water and also contain, in addition to the active ingredient and besides, if appropriate, a diluent or inert substance, wetting agents, for example polyoxyethylated fatty alcohols, alkyl- or alkylphenylsulfonates and dispersing agents, for example sodium lignin-sulfonate, sodium 2,2'-dinaphthylmethane-6,6'-disulfonate, sodium dibutylnaphthalenesulfonate or sodium oleyl-methyl-taurate. They are prepared in the customary manner, for example by grinding and mixing the components.

Emulsifiable concentrates can be prepared, for example, by dissolving the active ingredient in an inert organic solvent, for example butanol, cyclohexanone, dimethylformamide, xylene or higher-boiling aromatics or hydrocarbons, with addition of one or more emulsifiers. If the active ingredients are liquid, all or some of the solvent content can be dispensed with. Examples of emulsifiers which can be used are: calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensates, fatty alcohol/propylene oxide/ethylene oxide condensates, alkyl polyglycol ethers, sorbitan fatty acid esters, polyoxyethylene sorbitan fatty acid esters or polyoxyethylene sorbitol esters.

Dusting agents can be obtained by grinding the active ingredients with finely dispersed, solid substances, for example talc, or natural clays, such as kaolin, bentonite, pyrophillite or diatomaceous earth.

Granules can be prepared either by atomizing the active ingredient onto adsorbent, granular inert material, or by application of active ingredient concentrations to the surface of carriers, such as sand or kaolinites, or granular inert material by means of binders, for example polyvinyl alcohol, sodium polyacrylates or mineral oils. Suitable active ingredients can also be granulated in the manner customary for the preparation of fertilizer granules, if desired as a mixture with fertilizers.

In wetting powders, the active ingredient concentration is, for example, about 10 to 90% by weight, and the remainder to make up to 100% by weight consists of the customary formulation constituents. In the case of emulsifiable concentrates, the concentration of active ingredient is about 10 to 80% by weight. Dust-like formulations usually contain 5 to 20% by weight of active ingredient, and sprayable solutions contain about 2 to 20% by weight. in granules, the content of active ingredient depends partly on whether the active compound is present as a liquid or solid and on the granulation auxiliaries, fillers and the like used.

In addition, the active ingredient formulations mentioned contain, if appropriate, the particular customary tackifiers, wetting agents, dispersing agents, emulsifiers, penetration agents, solvents, fillers or carriers.

For application, the concentrates in the commercially available form are diluted, if necessary, in the customary manner, for example by means of water in the case of wettable powders, emulsifiable concentrates, dispersions and, in some cases, also microgranules. Dust-like and granular formulations and sprayable solutions are usually not diluted further with other inert substances before application.

Where relevant, mixtures or mixed formulations with other active ingredients, such as, for example, insecticides, acaricides, herbicides, fertilizers, growth regulators or fungicides, are also possible. Synergistic increases in action may in some cases be achieved, especially in mixtures with fungicides.

The application concentrations can be varied within wide limits, depending on the intended use and the time of application. Suitable concentrations for use as herbicides are between 0.3 and 10 kg/ha, preferably 0.5-3 kg/ha. The application concentrations are of course lower for use as growth regulators, and are about 0.1-2 kg/ha, it being possible for the required concentration to vary greatly, depending on the species of plant.

The invention is illustrated by the examples which follow.

(A) Preparation Examples

EXAMPLE 1

2-(Dimethylphosphinoyl)-2-hydroxy-acetic acid

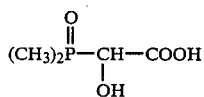

14.8 g (0.2 mol) of glyoxylic acid hydrate in 80 ml of ethyl acetate are added dropwise to a solution of 15.6 g (0.2 mol) of dimethylphosphine oxide in 80 ml of ethyl acetate. During this addition, the temperature rises slightly. The mixture is stirred at 25° C. for 24 hours and the product is filtered off with suction and washed with a little ethyl acetate to give, after drying, 20.2 g (66.5%) of the desired product of melting point 206°–208°.

EXAMPLE 2

Methyl 2-(dimethylphosphinoyl)-2-hydroxy-acetate

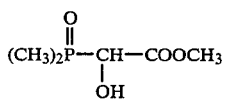

A solution of 17.6 g (0.2 mol) of methyl glyoxylate in 30 ml of dioxane is added dropwise to a solution of 15.6 g (0.2 mol) of dimethylphosphine oxide in 50 ml of dioxane. A spatula-tip of sodium methylate is added, the mixture is stirred at 25° C. for 24 hours and the evaporated residue is freed from adhering dioxane under a high vacuum and taken up in ethyl acetate to give, after trituration, 16.4 g (49.4%) of colorless product of melting point 84°–86°.

EXAMPLE 3

Ammonium 2-(dimethylphosphinoyl)-2-hydroxyacetate

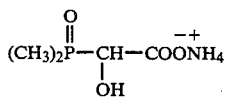

10 g of 25% strength aqueous ammonia solution are added dropwise to a solution of 15.2 g (0.1 mol) of 2-(dimethylphosphinoyl)-2-hydroxy-acetic acid in 10 ml of water. The temperature thereby rises to 38°. The mixture is stirred at 25° C. for one hour and concentrated on a rotary evaporator. The residue is first dehydrated azeotropically with toluene and then boiled up with acetonitrile. 14.3 g (84.6%) of the salt of melting point 183°–186° remain.

EXAMPLE 4

(a) Propylammonium 2-(dimethylphosphinoyl)-2-hydroxyacetate

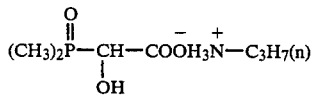

8.9 g (0.15 mol) of propylamine are added dropwise to a solution of 15.2 g (0.1 mol) of 2-(dimethylphosphinoyl)-2-hydroxy-acetic acid in 30 ml of water. The temperature thereby rises from 23° C. to 38° C. The mixture is stirred at 25° C. for one hour and concentrated on a rotary evaporator and the residue is dehydrated for distillation several times with toluene. After removal of the toluene under a high vacuum, a syrup of $n_D^{22}=1.4869$ initially forms, and solidifies as a wax after prolonged standing.

(b) The isopropylammonium salt, which is likewise obtained as a waxy substance, is prepared analogously.

EXAMPLE 5

Methyl 2-(dimethylphosphinoyl)-2-(methoxymethylcarbamoyloxy)-acetate

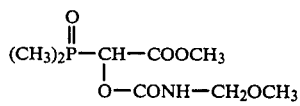

0.2 g of triethylamine is first added to a solution of 12.5 g (0.075 mol) of methyl 2-(dimethylphosphinoyl)-2-hydroxy-acetate in 50 ml of absolute dioxane, and 6.6 g (0.075 mol) of methoxymethyl isocyanate in 20 ml of absolute dioxane are then added dropwise. The mixture is stirred at 25° for 24 hours, the solvent is stripped off and the residue is recrystallized from diisopropyl ether-/ethyl acetate. 19.6 g (98%) of the desired product of melting point 101° are obtained.

EXAMPLE 6

2-(Dimethylphosphinoyl)-2-hydroxy-acetic acid hydrazide

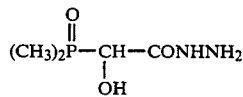

8.7 g (0.138 mol) of hydrazine hydrate (80% strength) are added dropwise to a solution of 21 g (0.0126 mol) of methyl 2-(dimethylphosphinoyl)-2-hydroxyacetate in 80 ml of ethanol such that the temperature does not exceed 25° C. The mixture is stirred at 25° C. for 14 hours and concentrated on a rotary evaporator and the residue is freed from adhering solvent under a high vacuum. After digestion with diisopropyl ether, 18.8 g (89.9%) of a colorless powder of melting point 152°–155° C. are obtained.

EXAMPLE 7

2-(Dimethylphosphinoyl)-2-hydroxy-acetamide

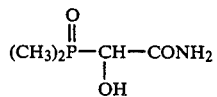

16.6 g (0.1 mol) of methyl 2-(dimethylphosphinoyl)-2-hydroxyacetate are dissolved in 70 ml of methanol, which has first been gassed with $NH_3$ gas for 10 minutes. After the mixture has been left to stand in a bomb tube at 25° for six days, it is filtered and concentrated and the oily residue is digested with ethyl acetate. 12.4 g (82.2%) of the amide of melting point 155° are obtained.

EXAMPLE 8

2-Hydroxy-methylphosphinoacetic acid

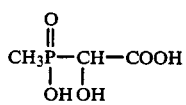

A solution of 44 g (0.5 mol) of methyl glyoxylate in 100 ml of ethyl acetate is added dropwise to a solution of 54 g (0.5 mol) of methanephosphonous acid monoethyl ester in 200 ml of ethyl acetate. The mixture is stirred at 25° for 24 hours and evaporated and residues of the solvent are removed under a high vacuum. 87 g of a syrup remain, and are warmed with 300 ml of concentrated HCl under reflux for 18 hours. The mixture is evaporated again, the residue is dehydrated azeotropically by stripping several times with toluene and residues of solvents are again removed under a high vacuum. The residue which remains crystallizes after being left to stand for several days. It is digested with ethyl acetate to give 26.8 g (34.8%) of a colorless powder of melting point 153°–157°.

EXAMPLE 9

Methyl 2-(dimethylphosphinoyl-2-chloro-acetate

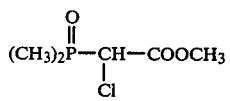

17.9 g (0.15 mol) of thionyl chloride in 20 ml of chloroform are added dropwise to a solution of 23.4 g (0.15 mol) of methyl 2-(dimethylphosphinoyl)-2-hydroxyacetate in 100 ml of chloroform, with ice-cooling, such that the temperature does not exceed 25° C. After 24 hours, the mixture is evaporated and the syrup which remains is freed from adhering solvent under a high vacuum. 25 g (100%) of a syrup which, according to the NMR, contains the desired compound in about 85% purity remain.

The following compounds are obtained analogously:

TABLE 1

$$\underset{R_2}{\overset{R_1}{\diagdown}}\underset{\parallel}{\overset{O}{P}}-A-\underset{\parallel}{\overset{O}{C}}-R_3$$

| Example No. | $R_1$ | $R_2$ | A | $R_3$ | Melting point (°C.) |
|---|---|---|---|---|---|
| 10 | —CH$_3$ | —CH$_3$ | —CH—OCONHCH$_3$ | —OCH$_3$ | 133 |
| 11 | —CH$_3$ | —CH$_3$ | —CH—OCONHC$_4$H$_9$(n) | —OCH$_3$ | syrup |
| 12 | —CH$_3$ | —CH$_3$ | —CH—OCONHCH$_2$COOC$_2$H$_5$ | —OCH$_3$ | 111 |
| 13 | —CH$_3$ | —CH$_3$ | —CH—OCONH—(2,4-Cl$_2$C$_6$H$_3$) | —OCH$_3$ | 291–193 |
| 14 | —CH$_3$ | —CH$_3$ | —CH—OCONHSO$_2$—CH—CH—CH$_3$ with CH$_3$ branch | —OCH$_3$ | 126–128 |
| 15 | —CH$_3$ | —CH$_3$ | —CH—OCONHSO$_2$—CH=CH—CH$_3$ | —OCH$_3$ | 185 |
| 16 | —C$_6$H$_5$ | —C$_6$H$_5$ | —CH—OH | —OH | 161–162 |
| 17 | —C$_6$H$_5$ | —C$_6$H$_5$ | —CH—OH | —OCH$_3$ | 159 |
| 18 | —C$_6$H$_5$ | —C$_6$H$_5$ | —CH—OH | —OC$_4$H$_9$(n) | 93 |
| 19 | —CH$_3$ | —C$_3$H$_7$(i) | —CH—OH | —OH | 149 |
| 20 | —C$_8$H$_{17}$(n) | —C$_8$H$_{17}$(n) | —CH—OH | —OCH$_3$ | syrup |
| 21 | —C$_8$H$_{17}$(n) | —C$_8$H$_{17}$(n) | —CH—OH | —OC$_4$H$_9$(u) | syrup |
| 22 | —CH$_2$C$_6$H$_5$ | —CH$_2$C$_6$H$_5$ | —CH—OH | —OH | 159 |
| 23 | —CH$_3$ | —CH$_3$ | —CH—Br | —OCH$_3$ | syrup |
| 24 | —CH$_3$ | —CH$_3$ | —CHNH$_2$ | —OH | syrup |
| 25 | —CH$_3$ | —CH$_3$ | —CHNH$_2$ | —O$^-$NH$_4^+$ | |
| 26 | —CH$_3$ | —CH$_3$ | —CHNH$_2$ | —O$^-$NH$_3^+$CH(CH$_3$)$_2$ | |
| 27 | —CH$_3$ | —CH$_3$ | —CHNH$_2$ | —OCH$_3$ | |
| 28 | —CH$_3$ | —CH$_3$ | —CHOCH$_3$ | —OCH$_3$ | |
| 29 | —CH$_3$ | —CH$_3$ | —CH—OCH$_2$C$_6$H$_5$ | —OCH$_3$ | |
| 30 | —CH$_3$ | —OH | —CH—NH$_2$ | —OH | |
| 31 | —CH$_3$ | —OH | —CH—NH$_2$ | —OCH$_3$ | |
| 32 | —C$_2$H$_5$ | —C$_2$H$_5$ | —CH—OH | —OH | 168–171 (decomp.) |

TABLE 1-continued $$\begin{array}{c} R_1 \\ \diagdown \\ P-A-C-R_3 \\ \diagup \\ R_2 \end{array} \begin{array}{c} O \\ \| \\ \end{array} \begin{array}{c} O \\ \| \\ \end{array}$$

| Example No. | $R_1$ | $R_2$ | A | $R_3$ | Melting point (°C.) |
|---|---|---|---|---|---|
| 33 | —$C_4H_9(n)$ | —$C_4H_9(n)$ | —CH—OH | —OH | 180 |
| 34 | —$C_4H_9(n)$ | —$C_4H_9(n)$ | —CH—OH | —$OC_4H_9(n)$ | syrup |
| 35 | —$C_4H_9(n)$ | —$C_4H_9(n)$ | —CH—OH | —$O^-N^+H_3C_3H_7(i)$ | syrup |
| 36 | —$CH_3$ | —$CH_3$ | —CH—OH | —$OC_3H_7(n)$ | |
| 37 | —$CH_3$ | —$CH_3$ | —CH—OH | —$OC_3H_7(i)$ | |
| 38 | —$CH_3$ | —$CH_3$ | —CH—OH | —$OC_6H_4CF_3(p)$ | |
| 39 | —$CH_3$ | —$CH_3$ | —CH—OH | —$OCH_2CH_2Cl$ | |
| 40 | —$CH_3$ | —$CH_3$ | —CH—OH | —$OCH_2CH_2CH_2Cl$ | |
| 41 | —$CH_3$ | —$CH_3$ | —CHOH | 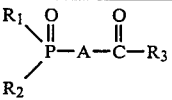 | |
| 42 | —$CH_3$ | —$CH_3$ | —CHOH |  | |

(B) Formulation Examples (a) A dusting agent is obtained by mixing 10 parts by weight of active ingredient and 90 parts by weight of talc or inert substance and comminuting the mixture in a hammer mill.

(b) A wettable powder which is readily dispersible in water is obtained by mixing 25 parts by weight of active ingredient, 64 parts by weight of kaolin-containing quartz, as the inert substance, 10 parts by weight of potassium lignin-sulfonate and 1 part by weight of sodium oleyl-methyl-taurate, as the wetting agent and dispersing agent, and grinding the mixture in a pinned disk mill.

(c) A dispersion concentrate which is readily dispersible in water is obtained by mixing 20 parts by weight of active ingredient with 6 parts by weight of alkylphenol polyglycol ether (Triton X 207), 3 parts by weight of isotridecanol polyglycol ether (8 mol of ethylene oxide) and 71 parts by weight of paraffinic mineral oil (boiling range, for example, about 255° to over 377° C.) and grinding the mixture to a fineness of less than 5 microns in a grinding bead mill.

(d) An emulsifiable concentrate is obtained from 15 parts by weight of active ingredient, 75 parts by weight of cyclohexanone, as the solvent, and 10 parts by weight of oxyethylated nonylphenol (10 mol of ethylene oxide), as the emulsifier.

(C) Biological Examples

EXAMPLE 1

Seeds or pieces of rhizome from graminaceous weeds and broad-leaved weeds were sown in sandy loam in plastic pots (φ 9 cm) and the weeds were grown under good growing conditions in a greenhouse for 3–5 weeks. The compounds according to the invention, formulated as wettable powders or aqueous solutions, were then sprayed onto the above-ground parts of the plants in the form of aqueous suspensions or sprayable solutions. The amount of water used thereby corresponded to 600–800 liters/ha. After standing in a greenhouse under optimum growing conditions for about 3 weeks, the herbicidal action was rated visually.

The results of the experiments with the novel compounds according to the invention are summarized in Table 1. The following code has been used:

0 = no action
1 = 0–20% action
2 = 20–40% action
3 = 40–60% action
4 = 60–80% action
5 = 80–100% action The values shown in Table 1 clearly document the very good herbicidal activity of the novel compounds against a broad spectrum of economically important harmful plants.

Abbreviations in Table 1:
SIA = *Sinapis arvensis*
AMR = *Amaranthus retroflexus*
STM = *Stellaria media*
AS = *Avena sativa*
ECG = *Echinochloa crus-galli*
LOM = *Lolium multiflorum*
a.i. = active ingredient

TABLE 1

| | Herbicidal action in the post-emergence method | | | | | | |
|---|---|---|---|---|---|---|---|
| | Dose | Herbicidal action | | | | | |
| Example | a.i./ha | SIA | AMR | STM | AS | ECG | LOM |
| 6 | 10 | 5 | 3 | 5 | 3 | 5 | 5 |
| 11 | 10 | 5 | 5 | 4 | 4 | 4 | 4 |
| 14 | 10 | 5 | 5 | 5 | 5 | 5 | 5 |
| 1 | 10 | 5 | 5 | 5 | 5 | 5 | 5 |
| 3 | 10 | 5 | 5 | 5 | 5 | 5 | 5 |
| 4a | 10 | 5 | 5 | 5 | 5 | 5 | 5 |
| 2 | 10 | 5 | 5 | 5 | 5 | 5 | 5 |
| 4b | 10 | 5 | 5 | 5 | 5 | 5 | 5 |

EXAMPLE 2

Sugar cane plants in the open were sprayed with aqueous suspensions of emulsion concentrates of the comparison compounds in various concentrations. After 4 and 8 weeks, plants were taken and investigated for their content of sugar cane (sucrose) (by means of the so-called "press method", T. Tanimoto, Hawaiian Planters Record 57, 133 (1964)).

The sugar content is thereby determined polarimetrically and expressed in "pol. percent cane"; this figure corresponds to the percentage of sucrose in the solution, on the assumption that sucrose is the only substance in the sugar solution which rotates the plane of polarized light. The determination of the "pol. % cane" is a recognized method of determining the sugar content of cane sugar.

The results are summarized in the following Table 2

TABLE 2

| | Amount applied kg of a.i./ha | Sucrose content (pol. % cane) Weeks after treatment | |
|---|---|---|---|
| | | 4 | 8 |
| Compound I Example No. 1 | 2.5 | 13.9 | 14.8 |
| Compound II Example No. 14 | 2.5 | 12.4 | 13.3 |
| Control (untreated) | — | 10.0 | 11.2 |

We claim:

1. A compound of the formula

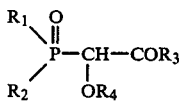

and salts thereof with bases and acids in which
$R_1$ is $C_1$ or $C_2$-alkyl and $R_2$ is $C_1$-alkyl;
$R_3$ is —OH, $(C_1-C_{12})$-alkoxy, $(C_3-C_8)$-cycloalkoxy, $(C_3-C_6)$-alkenyloxy, $(C_3-C_6)$-alkynyloxy, phenoxy or benzyloxy, it being possible for the groups mentioned in turn to be substituted by OH, halogen, $CF_3$, $(C_1-C_4)$-alkyl or $(C_1-C_4)$-alkoxy, or $R_3$ is hydrazino;
$R_4$ is H, $(C_1-C_6)$-alkyl, allyl, propargyl, benzyl, halogenobenzyl or $CONR_4R_6$;
$R_5$ and $R_6$ independently of one another are hydrogen, $(C_1-C_{12})$-alkyl, $(C_3-C_8)$-cycloalkyl, $(C_3-C_6)$-alkenyl, $(C_3-C_6)$-alkynyl, phenyl, benzyl, benzoyl, phenoxysulfonyl, $(C_1-C_{12})$-alkylsulfonyl, $(C_3-C_6)$-alkenylsulfonyl or phenylsulfonyl, it being possible for the groups mentioned in turn to be substituted by halogen, $CF_3$, CN, $(C_1-C_4)$-alkoxy or $(C_1-C_4)$-alkoxycarbonyl.

2. The compound as claimed in claim 1, wherein $R_1$ and $R_2$ are methyl.

3. A compound as claimed in claim 1, wherein $R_1$ and $R_2$ are methyl, $R_3$ is —OH or —O—$(C_1-C_{10})$-alkyl and $R_4$ is H, of if $R_3$=OH, a salt of such a compound.

4. 2-(Dimethylphosphinoyl)-2-hydroxyacetic acid or its methyl ester or its ammonium or $(C_1-C_4)$-alkylammonium salt.

5. A herbicidal and growth-regulating agent, which contains a compound of claim 3 with a carrier therefor.

6. A method for combating undesirable plant growth, which comprises treating affected areas with an effective amount of a compound as claimed in claim 3.

7. A method for controlling plant growth and plant development and of increasing the amount of desirable plant contents in useful plants, which comprises treating the plants with an effective amount of a compound as claimed in claim 3.

8. A herbicidal and growth-regulating agent which contains a compound of the formula:

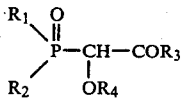

and salts thereof with bases and acids in which
$R_1$ and $R_2$ independently of one another are $C_1$ or $C_2$-alkyl; $R_3$ is —OH, $(C_1-C_{12})$-alkoxy, $(C_3-C_8)$-cycloalkoxy, $(C_3-C_6)$-alkenyloxy, $(C_3-C_6)$-alkynyloxy, phenoxy or benzyloxy, it being possible for the groups mentioned in turn to be substituted by OH, halogen, $CF_3$, $(C_1-C_4)$-alkyl or $(C_1-C_4)$-alkoxy, or $R_3$ is hydrazino;
$R_4$ is H, $(C_1-C_6)$-alkyl, allyl, propargyl, benzyl, halogenobenzyl or $CONR_5R_6$;
$R_5$ and $R_6$ independently of one another are hydrogen, $(C_1-C_{12})$-alkyl, $(C_3-C_8)$-cycloalkyl, $(C_3-C_6)$-alkenyl, $(C_3-C_6)$-alkynyl, phenyl, benzyl, benzoyl, phenoxysulfonyl, $(C_1-C_{12})$-alkylsulfonyl, $(C_3-C_6)$-alkenylsulfonyl or phenylsulfonyl, it being possible for the groups mentioned in turn to be substituted by halogen, $CF_3$, CN, $(C_1-C_4)$-alkoxy or $(C_1-C_4)$-alkoxycarbonyl with a carrier therefor.

9. A method for combating undesirable plant growth, which comprises treating affected areas with an effective amount of a compound of the formula

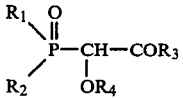

and salts thereof with bases and acids in which
$R_1$ and $R_2$ independently of one another are $C_1$ or $C_2$-alkyl; $R_3$ is —OH, $(C_1-C_{12})$-alkoxy, $(C_3-C_8)$-cycloalkoxy, $(C_3-C_6)$-alkenyloxy, $(C_3-C_6)$-alkynyloxy, phenoxy or benzyloxy, it being possible for the groups mentioned in turn to be substituted by OH, halogen, $CF_3$, $(C_1-C_4)$-alkyl or $(C_1-C_4)$-alkoxy, or $R_3$ is hydrazino;
$R_4$ is H, $(C_1-C_6)$-alkyl, allyl, propargyl, benzyl, halogenobenzyl or $CONR_5R_6$;
$R_5$ and $R_6$ independently of one another are hydrogen, $(C_1-C_{12})$-alkyl, $(C_3-C_8)$-cycloalkyl, $(C_3-C_6)$-alkenyl, $(C_3-C_6)$-alkynyl, phenyl, benzyl, benzoyl, phenoxysulfonyl, $(C_1-C_{12})$-alkylsulfonyl, $(C_3-C_6)$-alkenylsulfonyl or phenylsulfonyl, it being possible for the groups mentioned in turn to be substituted by halogen, $CF_3$, CN, $(C_1-C_4)$alkoxy or $(C_1-C_4)$-alkoxycarbonyl.

10. A method for controlling plant growth and plant development and of increasing the amount of desirable plant contents in useful plants, which comprises treating the plants with an effective amount of a compound of the formula

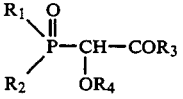

and salts thereof with bases and acids in which $R_1$ and $R_2$ independently of one another are $C_1$-$C_2$-alkyl; $R_3$ is —OH, ($C_1$-$C_{12}$)-alkoxy, ($C_3$-$C_8$)-cycloalkoxy, ($C_3$-$C_6$)-alkenyloxy, ($C_3$-$C_6$)-alkynyloxy, phenoxy or benzyloxy, it being possible for the groups mentioned in turn to be substituted by OH, halogen, $CF_3$, ($C_1$-$C_4$)-alkyl or ($C_1$-$C_4$)-alkoxy, or $R_3$ is hydrazino;

$R_4$ is H, ($C_1$-$C_6$)-alkyl, allyl, propargyl, benzyl, halogenobenzyl or $CONR_5R_6$;

$R_5$ and $R_6$ independently of one another are hydrogen, ($C_1$-$C_{12}$)-alkyl, ($C_3$-$C_8$)-cycloalkyl, ($C_3$-$C_6$)-alkenyl, ($C_3$-$C_6$)-alkynyl, phenyl, benzyl, benzoyl, phenoxysulfonyl, ($C_1$-$C_{12}$)-alkylsulfonyl, ($C_3$-$C_6$)-alkenylsulfonyl) or phenylsulfonyl, it being possible for the groups mentioned in turn to be substituted by halogen, $CF_3$, CN, ($C_1$-$C_4$)-alkoxy or ($C_1$-$C_4$)-alkoxycarbonyl.

11. A herbicidal and growth-regulating agent, which contains 2-(Dimethylphosphinoyl)-2-hydroxyacetic acid or its methyl ester or its ammonium or ($C_1$-$C_4$)-alkylammonium salt with a carrier therefor.

12. A method for combating undesirable plant growth which comprises treating affected areas with an effective amount of 2-(Dimethylphosphinoyl)-2-hydroxyacetic acid or its methyl ester or its ammonium or ($C_1$-$C_4$)-alkylammonium salt.

13. A method for controlling plant growth and plant development and of increasing the amount of desirable plant contents in useful plants which comprises treating the plants with an effective amount of 2-(Dimethylphosphinoyl)-2-hydroxyacetic acid or its methyl ester or its ammonium or ($C_1$-$C_4$)-alkylammonium salt.

* * * * *